United States Patent [19]

Leak et al.

[11] 4,181,024
[45] Jan. 1, 1980

[54] HELICOPTER ROTOR SYSTEM RELATED VIBRATION AMPLITUDE DETECTING SYSTEM

[75] Inventors: John Leak, Swarthmore; Aaron Miller, Jr., Aston, both of Pa.

[73] Assignee: The Boeing Company, Seattle, Wash.

[21] Appl. No.: 933,949

[22] Filed: Aug. 15, 1978

[51] Int. Cl.$^2$ ............................................. G01N 29/00
[52] U.S. Cl. ..................................................... 73/660
[58] Field of Search .................. 73/660, 658, 659, 455

[56] References Cited

U.S. PATENT DOCUMENTS

| | | | |
|---|---|---|---|
| 3,386,031 | 5/1968 | Able et al. | 73/455 |
| 3,945,256 | 3/1976 | Wilson et al. | 73/455 |
| 4,053,123 | 10/1977 | Chadwick | 73/455 |

Primary Examiner—Anthony W. Ciarlante
Attorney, Agent, or Firm—Felix J. D'Ambrosio; Edwin E. Greigg; Jack D. Puffer

[57] ABSTRACT

What follows is a description of a system for detecting rotor system related vibration in a helicopter. The vibration detecting system comprises three essential units: a sensing unit or device; a control unit; and a model module. Actually, any number of sensing units can be utilized depending upon the number of locations at which the vibration is to be monitored. The sensing unit generates a signal indicative of the rotor system related vibration and delivers this signal to the control unit which operates on the generated signal and produces an output signal within a selected frequency and amplitude range. The output signal is then displayed, for example, on a scale meter. The model module is adaptable for compatibility with the dynamic rotor system of a given helicopter model and is utilized as such to set the limits of the selected frequency and amplitude range of the control unit. The model module is readily connected to and removed from the housing of the control unit.

16 Claims, 7 Drawing Figures

U.S. Patent  Jan. 1, 1980  Sheet 1 of 5  4,181,024
FIG.1
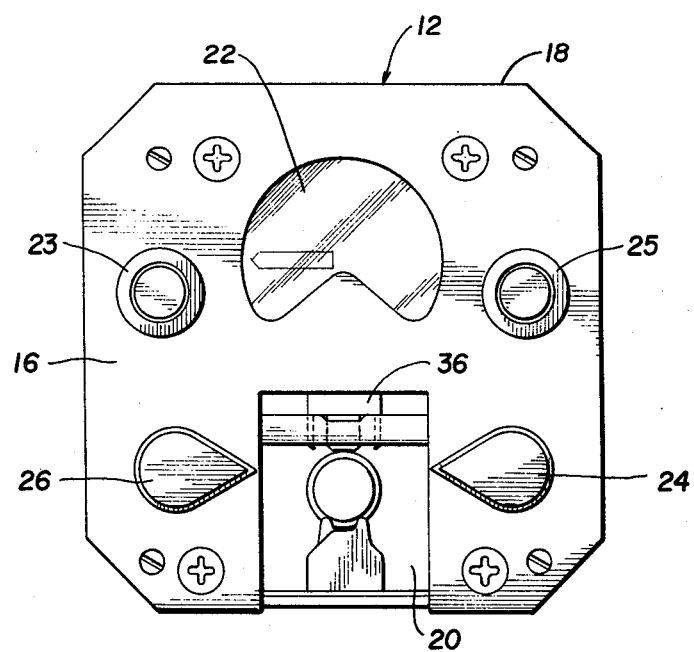
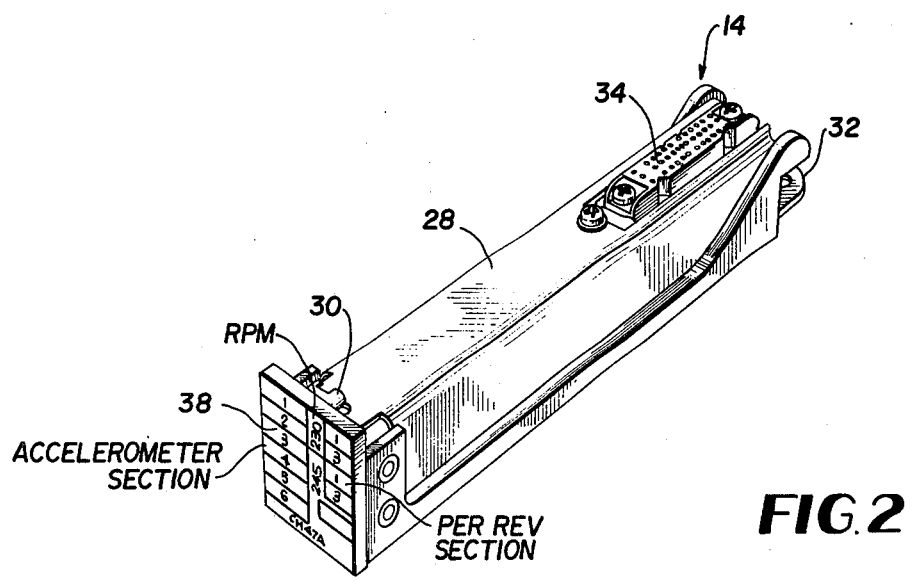
FIG.2

HELICOPTER ROTOR SYSTEM RELATED VIBRATION AMPLITUDE DETECTING SYSTEM

BACKGROUND OF THE INVENTION

This invention relates to helicopter rotor system related vibration amplitude detecting systems.

The use of some form of rotor frequency related vibration amplitude detector has been standard practice in production flight testing at the Boeing Vertol Company, to whom this application is assigned, since 1965. Initially, oscillographic recording of accelerometer signals was used which precluded in-flight observation. Later a tuned reed technique was developed for that model helicopter designated as the CH 46. This technique was restricted, however, to a unique frequency and amplitude.

An electronic vibration amplitude detecting system was next developed by the Boeing Vertol Company for that model helicopter designated as the CH 47A. The system utilized passive filters to select the required harmonic from servo accelerometer signals. This system was later adapted and modified for use on the CH 47B and CH 47C helicopters. A similar system was also developed for the CH 46 helicopter.

Although these systems had a much greater utility than their predecessor systems, they still suffered from a lack of flexibility in that each unit was designed for a specific helicopter model and required major rework if they were to be interchanged. This lack of flexibility caused significant flight delays due to the need to rework the system of one model helicopter for use on another model helicopter when supplies for the latter model helicopter were low.

It would be desirable, therefore, to have a vibration amplitude detecting system which is flexible and useable on all helicopter models, presently existing as well as future models.

OBJECTS AND SUMMARY OF THE INVENTION

It is, therefore, an object of this invention to provide a vibration amplitude detecting system which can be readily adapted for use in any make or model helicopter.

It is a related object of this invention to provide a vibration amplitude detecting system which is relatively compact and easy to install and remove.

These objects are achieved by the provision of a vibration amplitude detecting system having three essential units: a sensing unit(s) or device(s); a control unit; and a model module. The model module is provided with circuitry adapted to a particular model helicopter and when electrically connected to the control unit in turn adapts the control unit to the particular model helicopter.

For ease of assembly, the control unit includes a housing with a trough or slot into which the model module is received and mounted to effect the electrical connection. The mounting structure on both the control unit and model module are designed for ready connection and removal.

The model module can be adapted to a particular model helicopter because the rotor systems of different model helicopters are in many ways different so that the dynamic response of these rotor systems are unique. We have found that one way to achieve our objectives is to utilize a band-pass filter in the control unit whose operation is altered by the particular model module connected in circuit with the control unit.

BRIEF DESCRIPTION OF THE DRAWINGS

FIG. 1 is a front elevation view of the control unit housing with a trough or slot for receiving a model module.

FIG. 2 is a perspective view of a model module housing illustrating the connector for electrically connecting the model module circuitry to the control unit circuitry and the structure for mounting and securing the model module to the control unit.

DESCRIPTION OF THE PREFERRED EMBODIMENT

Figure 3:
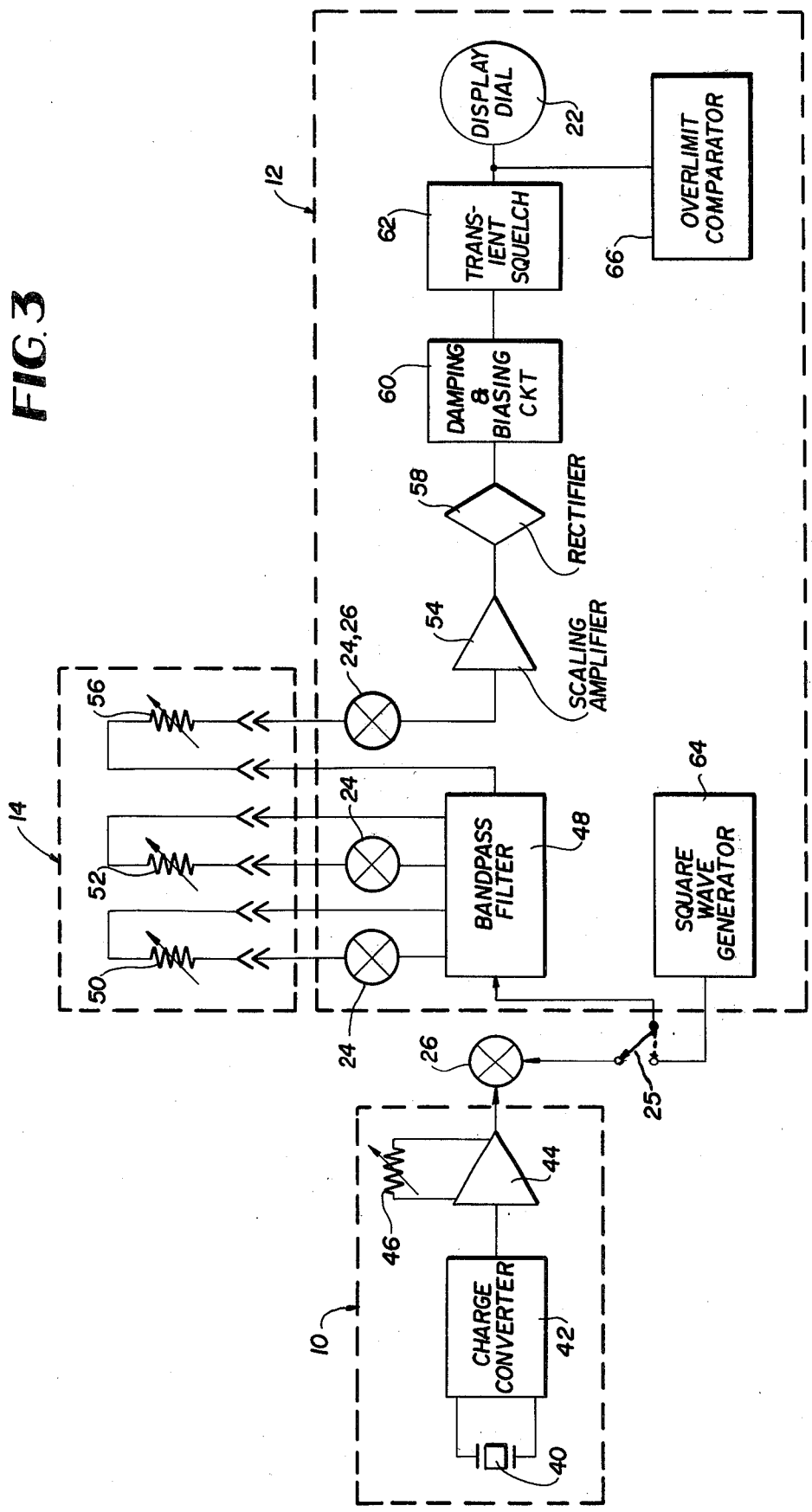
FIG. 3 is a circuit block diagram of the vibration amplitude detecting system according to the invention.

The vibration amplitude detecting system comprises three essential units: a vibration amplitude sensing unit or device 10 (FIGS. 3 and 4A); a control unit 12; and a model module 14.

A front panel 16 of a control unit housing 18 is shown in FIG. 1 as well as a trough or slot 20, display dial 22 which is preferably scaled in percentage and is graduated from 30% to 150%, a power on-off switch 23, a system check switch 25, and multi-position gang switches 24 and 26.

Figure 5:
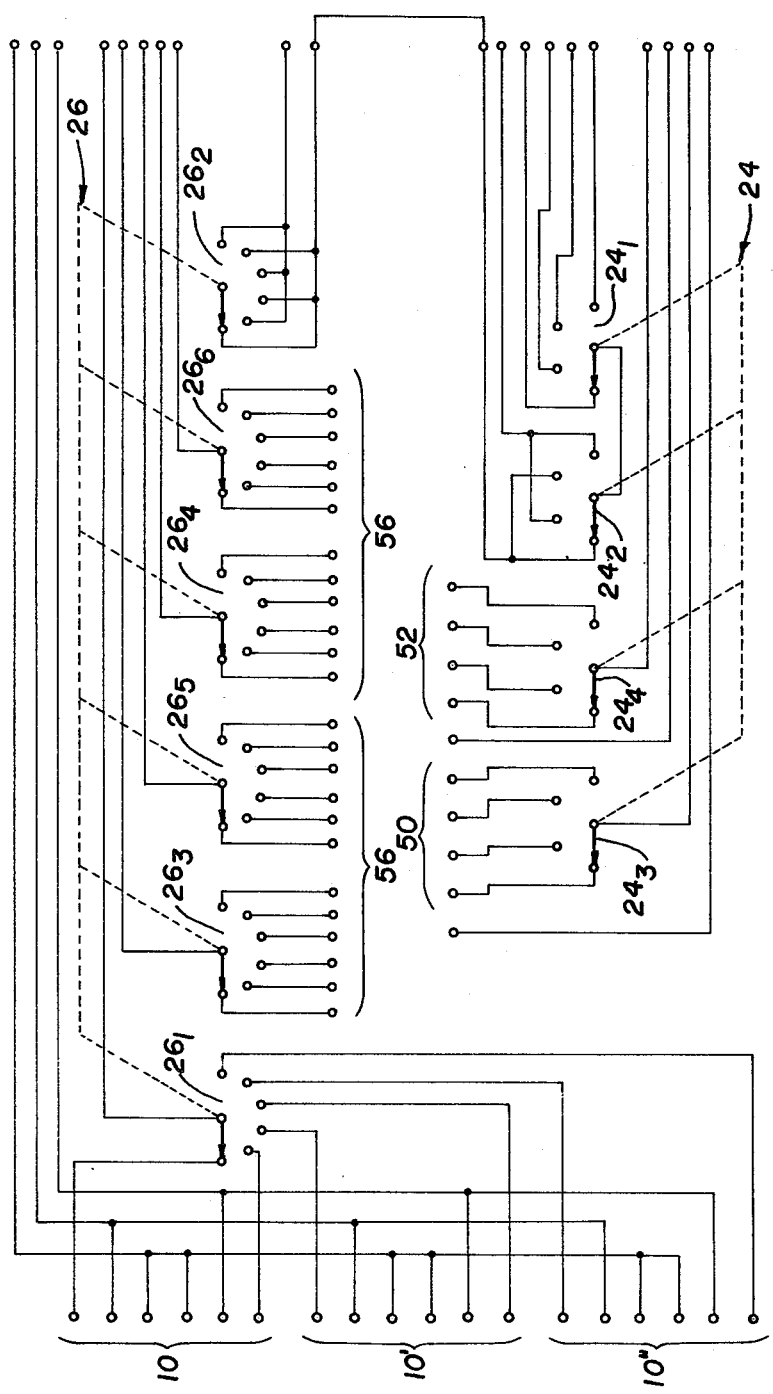
FIG. 5 is a wiring diagram illustrating the functional relationship of the switches 24 and 26.
Figure 6:
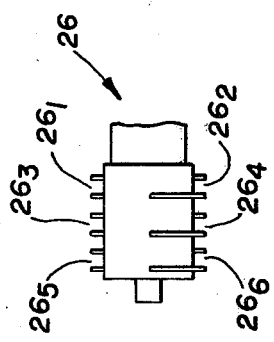
FIG. 6 is a side view of switch 26. Switch 24 is similarly constructed.

According to a preferred embodiment, the control unit is 3.25 in. square, 8.75 in. long and weighs approximately 2 lbs. It is fabricated from aluminum. The panel 16 incorporates a mask which uncovers a warning flag at a reading on the display dial 22 of 100% and over. The system check switch 25 (first selector means) incorporates an over limit warning circuit which may include a light which lights at a scale reading of 125% and stays on until the reading drops below 100%. The switches 24 and 26 (second selector means) are shown in FIG. 1 as single multi-position switches, while in FIGS. 3-5, their operative interconnection is shown. The operation of these switches will be better understood from the description that follows of the circuit block diagram of FIG. 3, in conjunction with the references to the circuit diagrams of FIGS. 4A, 4B and 5 and the side view of FIG. 6.

All the active electronic circuits are mounted on four printed circuit cards which are mounted in housing 18. One of the circuit cards acts as a carrier for the other three circuit cards and as a connection matrix for the switches and external connectors.

FIG. 2 illustrates a typical model module 14. The module includes a housing 28 within which six groups of variable resistors are mounted (FIG. 4B) on two printed circuit cards, and from which the resistances 50, 52 and 56 (FIG. 3) are selected. According to a preferred embodiment, the model module is 1 in. square, 6.5 in. long and weighs approximately 0.3 lbs. It is fabricated also from aluminum. The model module 14 is dimensioned to be readily received within and removed from the slot 20 of the control unit 12, and is secured therein by a front pin 30 and a Camloc fastener 32.

When the model module 14 is secured in this fashion within the slot 20, a connector 34 engages a connector 36 (FIG. 1) to effect the necessary electrical connection between the various circuits in the two units. The connector 36 includes a plurality of pins for receiving a corresponding plurality of pin slots located on the connector 34. The pins and slots are aligned by the pin 30 and Camloc 32 during the course of securing the model module to the control unit. The model module 14 is readily inserted and removed from the control unit 12 with the pin and Camloc design.

The model module housing 28 has a front panel 38 which is flush with the front panel 16 of the control unit when the model module is secured to the control unit. The indicia on the front panel 38 complements that on the front panel 16 and serves as an identification table.

Figure 4A:
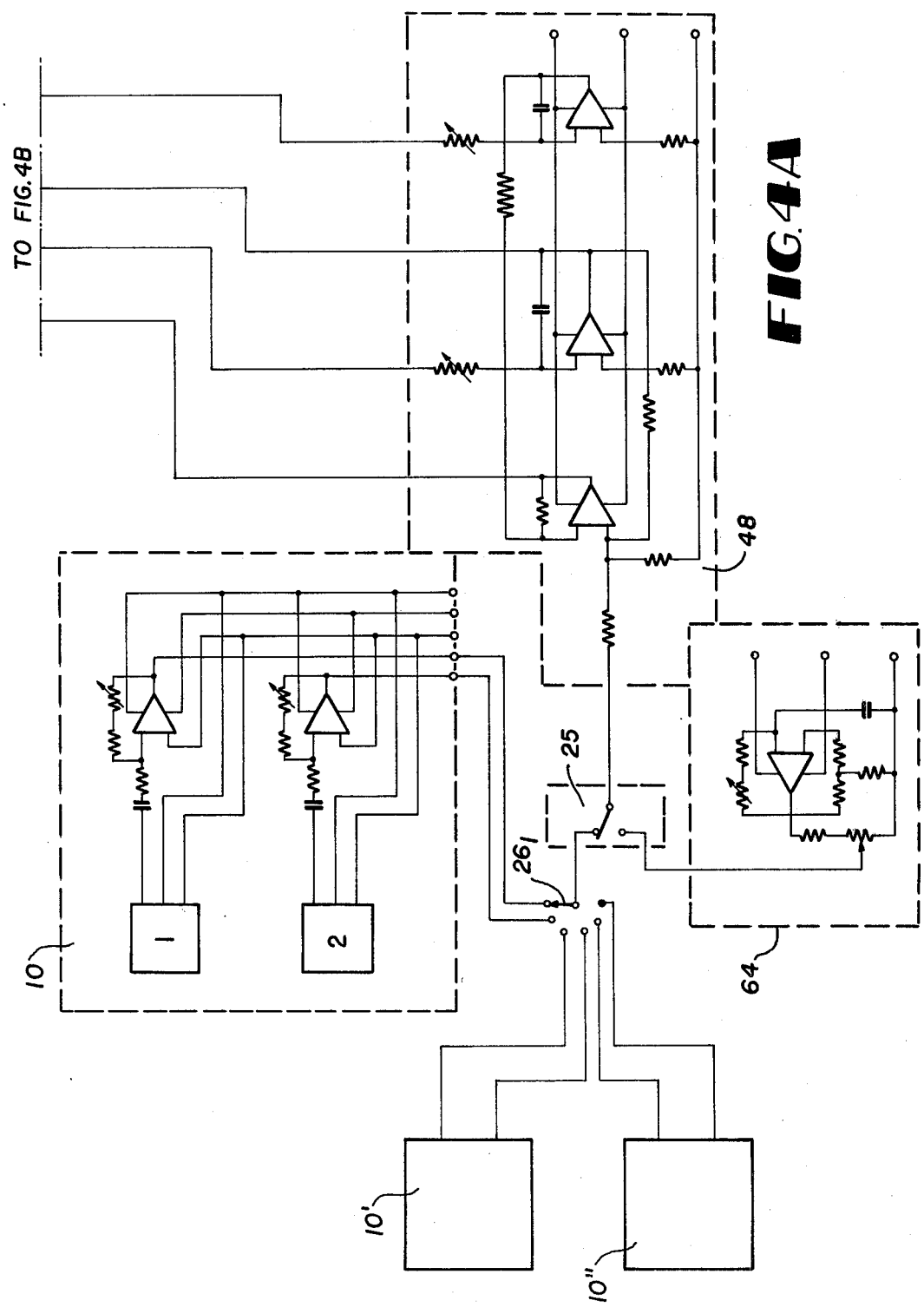
FIGS. 4A and 4B together illustrate a detailed circuit diagram of the vibration amplitude detecting system according to the invention.

A vibration amplitude sensing device 10 is not shown in FIGS. 1 and 2 because it is not part of the control unit-model module package. A sensing device is located on the helicopter in the vibrational sphere of the rotor system related vibration, and is connected to the control unit by a suitable electrical cable. If desired, more than one sensing device can be employed (as shown in FIG. 4A) at different locations on the helicopter, all suitably electrically connected to the control unit, and specifically to switch 26. In the preferred embodiment the number of sensing devices is limited to three.

Each sensing unit package is preferably 3 in. cube, weighing 1.2 lbs. and contains two accelerometers with their sensitive axes at right angles, so that the unit can sense vibrations on any two rectilinear axes.

The control unit and model module assembly is mounted, preferably on the pilot control panel within the helicopter cockpit. As an assembly, it too is easily inserted and removed from the pilot control panel.

In FIG. 3 each of the essential three units, the circuits associated with the sensing device 10; the control unit 12; and the model module 14, are shown. As noted above, any number of sensing devices can be employed. For the sake of clarity, only one device with one accelerometer and associated circuitry is shown in FIG. 3. If more than one sensing device is used it can be connected to the control unit 12 by the multi-position switch 26. (See FIGS. 4A, 4B and 5.)

In the sensing device 10, a vibration signal is generated by a piezo-electric accelerometer 40. Only one accelerometer of the pair is operated at a given time by the switch 26, although the operation of each accelerometer is similar. This generated signal is fed through a charge converter 42 to a variable gain amplifier 44. The gain of the amplifier 44 is set by means of a variable resistor 46, the purpose of which is to compensate for differences in the transfer functions of individual accelerometers and provide a normalized signal. In this way, it is possible to change accelerometer-amplifier subsystems without compromising the scaling accuracy. The normalized vibration signal is then fed through the switches 26 and 25 to the control unit 12 where it is operated upon and an output signal produced, with indicia thereof being displayed on the display dial 22.

Figure 4B:
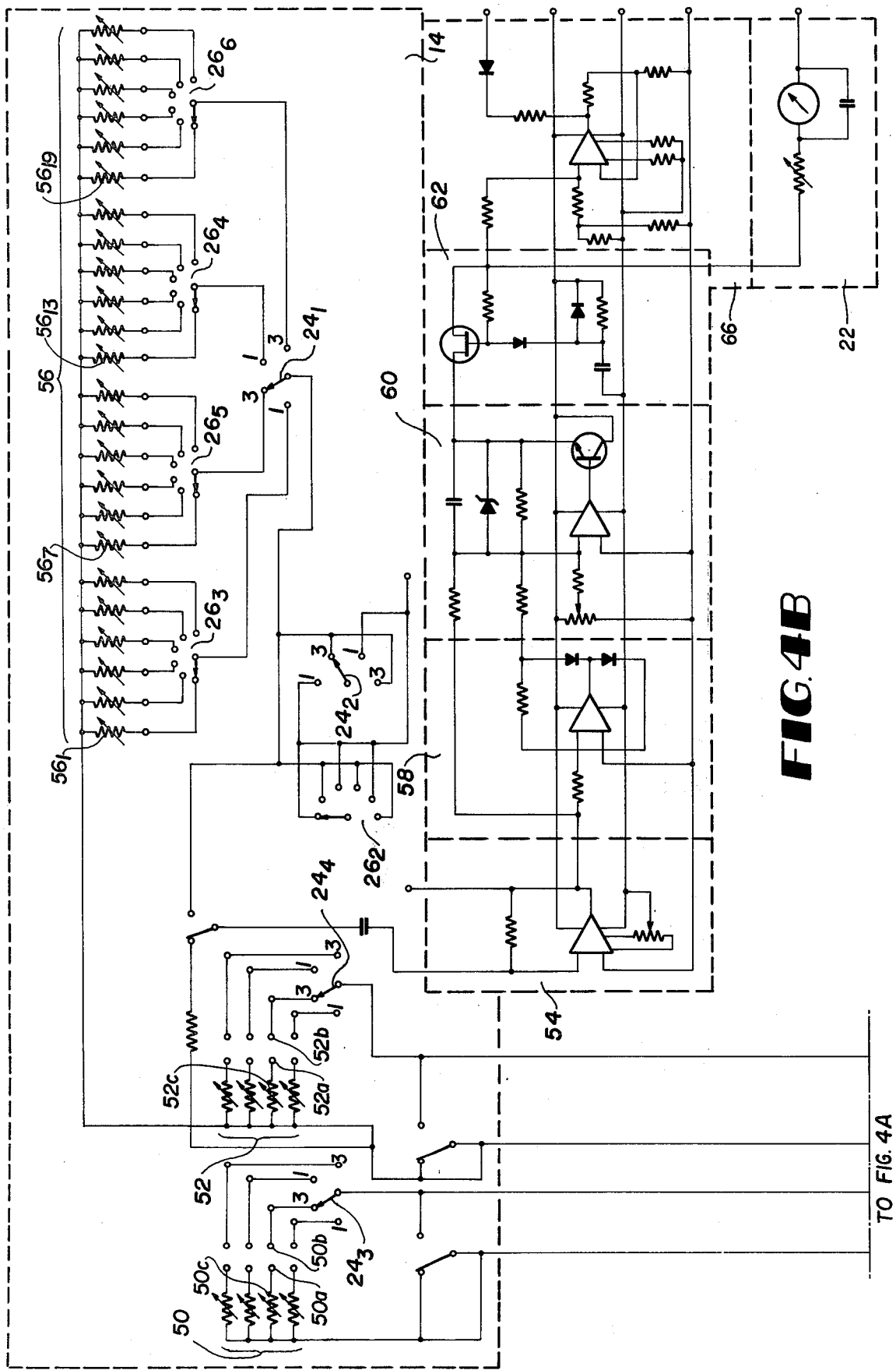

The normalized vibration signal is fed to a tuned band-pass filter 48, the centerband frequency of which is controlled by a selected pair of variable resistances 50 and 52, which are selected from a group if 8-100 Kohm variable resistors mounted in the model module 14. These variable resistors are in series with fixed resistors (not shown) connectable across the terminals 50a, 50b; 52a, 52b (FIG. 4B). These resistors are electrically connected to the filter 48 by the multi-position switch 24, which in the preferred embodiment is limited to four positions with variance in each position (see FIGS. 4A, 4B and 5). Both of the selected resistances are connected to the filter 48.

The filter output, consisting essentially of one discrete frequency component of the general vibration signal, is fed to a variable gain scaling amplifier 54, the gain of which is controlled by a selected input resistance 56, which is selected by the switches 24 and 26 (FIGS. 4A, 4B and 5) from a group of 24-100 Kohm resistors mounted in the model module 14. The value of the selected resistance 56 is determined by the specified limiting level of vibration at the given frequency and accelerometer location.

The output of the amplifier 54 is converted to a d.c. voltage by a full-wave rectifier circuit 58, the resulting signal being used to drive a damping and biasing circuit 60. The purpose of this circuit is twofold: first, it contains an inductive network having a time constant sufficiently high to obliterate signal transients caused by short-term instabilities (due, for instance, to wind gusts) at the accelerometer. Secondly, it contains a biasing circuit which cuts out the signal when it falls below a certain amplitude. This compensates for the known nonlinearity of the rectifier at low signal levels.

The damper and biasing circuit 60 drives the display dial 22.

Between circuit 60 and the display dial 22 is located a power transient squelch circuit 62. This circuit consists essentially of a field effect transistor connected into the signal circuit and also into the main system power supply through an inductive time-delay circuit (see FIG. 4B). Its purpose is to provide an effective open circuit between circuit 60 and the display 22 until a predetermined time after the application of power to the system, at which time the circuit is closed and the system becomes operational. This blocks signal transients caused by momentary instabilities of the system components at the time of power application from reaching and possibly damaging the display.

In parallel with the display dial 22 is a overlimit comparator and a overlimit indicator 66. This circuit consists of an operational amplifier in a comparator configuration. The reference input is derived from the regulated power supply and is equivalent to 125% display dial indication. When the input to the display dial exceeds 125% the comparator energizes the overlimit indicator. Hystersis in the comparator circuit holds the overlimit indicator energized until the input drops below the 100% level.

All the resistive components required to control the filter tuning and scaling amplifier gain are contained in the model module 14. The model module 14 can, therefore, be readily adapted to any specified set of frequencies and amplitudes peculiar to a given aircraft, as will be demonstrated hereinafter.

It is desirable to be able to check that the system is operating correctly while it is in use. To do this, a free-running multi-vibrator (square wave generator) 64 set to a specific frequency and amplitude is included in the system. Switch 25 is used to replace the accelerometer signal with this square wave (see FIG. 4A), which follows the path defined above and registers a specified reading on the display dial 22, thus confirming that all circuits except the accelerometers are working correctly.

To calibrate a model module for a particular aircraft and the three sensing units mounted to the aircraft, the following relationships have been developed empirically:

(1) $R_1 = 302/SN$ (megohms)
(2) $R_2 = (6328 g^2 - 116312/S^2N^2)^{1/2}$ (Kohms) where:
$R_1$ = tuning resistance (resistors 50 and 52)
$R_2$ = amplitude resistance (resistors 56)
S = rotor speed (rpm)
N = per-rev harmonic
g = specified maximum vibration amplitude For any given aircraft, acceptable vibration amplitudes are determined during flight testing for the various dynamic systems of the aircraft. Therefore, acceptable maximum vibration amplitudes (g) are known. Knowing the acceptable amplitudes (g) at each accelerometer location, the operating rotor speed (S) and harmonics (N), the values of $R_1$ and $R_2$ can be determined. For example, assuming an acceptable vibration amplitude of 0.2 g at the location of accelerometer 1 (FIG. 4A), a 3 per-rev harmonic (N) and a rotor speed of 230 rpm (S), the values of $R_1$ and $R_2$ are calculated to be as follows:

$$R_1 = 302/(230)(3) = 438 \text{ Kohm}$$

$$R_2 = [(6328)(0.2)^2 - 116312/(230)^2(3)^2]^{\frac{1}{2}} = (253.12 - 116312/476100)^{\frac{1}{2}} = (252.88)^{\frac{1}{2}} = 15.9 \text{ Kohm}$$

With these values of $R_1$ and $R_2$ the values of resistances 50, 52 and 56 are set as follows: a fixed resistor of 400 Kohm is placed across terminals 50a, 50b and another across terminals 52a, 52b; the variable resistances 50c and 52c are set to 38 Kohms; and the resistance $56_7$ is set to 15.9 Kohm. This procedure is followed in adjusting the remaining resistances 50, 52 and 56 for all the possible combinations of accelerometers, rpm and harmonics. Since, for practical purposes, there are six accelerometers, two operating rpm ranges (230 and 245) and two harmonics (1 per-rev and 3 per-rev), twenty-four resistors ($56_1$–$56_{24}$) comprise the resistance 56. Each of these twenty-four resistors, therefore, is assigned to a respective accelerometer, rpm and harmonic. Resistors $56_7$–$56_{12}$ are assigned to accelerometers 1–6, respectively, for an rpm of 230 and a 3 per-rev harmonic. Resistors $56_{13}$–$56_{19}$ are assigned to accelerometers 1–6, respectively, for an rpm of 245 and a 1 per-rev harmonic, etc. Once all the resistance values have been set, the model module housing 28 is installed and the unit is ready for use. An aircraft designation is placed on the front panel 38 to identify the unit module.

If, at any time during the service life of the aircraft, a particular vibration is to be monitored, the model module for that aircraft is inserted in the slot 20 of control unit 12. Assuming that the vibration to be monitored is a 3 per-rev harmonic which is detected by accelerometer 1 of te sensing unit 10, and assuming further that the aircraft is to operate at 230 rpm, then the pilot simply adjusts switch 26 to position 1 on the panel 38 and adjusts switch 24 to the 3 per-rev and 230 rpm position on the panel 38. These adjustments produce the switch positions shown in FIGS. 4A and 4B. By the adjustment of switches 24 and 26, the filter 48 and amplifier 54 are adjusted. Next the pilot connects the switch 25 to the generator 64, thereby connecting the generator 64 to the control unit 12. If a reading of 100% appears on the display dial 22, then the system is functioning properly. During flight, with the rotor turning at 230 rpm, the switch 25 is connected to switch 26 which connects accelerometer 1 of sensing unit 10 to the control unit 12. A reading in excess of 100% indicates that the vibration level being monitored exceeds acceptable levels.

The vibration amplitude detection system described is more flexible than any of the known systems because the model module can easily be recalibrated for any aircraft model and for as many sensors as desired.

What is claimed is:

1. A helicopter rotor system related vibration amplitude detecting system, comprising in combination;
at least one vibration amplitude sensing device mounted to the helicopter in the vibrational sphere of the rotor system related vibration, said sensing device generating a signal which is indicative of the amplitude of the rotor system related vibration; a control unit having a housing including: first selector means; second selector means connected to the first selector means and connectable to each sensing device for selectively, electrically connecting each sensing device to said first selector means, said first selector means serving to selectively receive the generated signal from each sensing device; electrical control means for operating on the selected generated signal and producing an output signal within a selected frequency and amplitude range; display means for displaying indicia of the output signal; a receiving slot for a model module; and mounting means for a connector within the receiving slot; and
a model module having a housing which is received within the receiving slot, said model module housing including: mounting means which engage the control unit mounting means for securing the model module to the control unit; a connector which engages the control unit connector for electrically connecting the model module to the second selector means; and electrical means selectively applied to the electrical control means by said second selector means for determining the selected frequency and amplitude range.

2. The combination as defined in claim 1, wherein the electrical means of said model module include variable resistors which are preset as a function of the dynamic rotor system of the helicopter.

3. The combination as defined in claim 2, wherein the electrical control means includes filter means, electrically connected to said first selector means for receiving the generated signal of a selected sensing device and to said second selector means for adapting the filter means to the dynamic rotor system of the helicopter.

4. The combination as defined in claim 3, wherein the electrical control means further includes: a scaling amplifier electrically connected to said second selector means and thereby to a variable resistor in the model module for controlling the gain thereof, said scaling amplifier receiving the output from said filter means; a full-wave rectifier circuit which receives the output from said scaling amplifier; and a damping and biasing circuit which receives the output from the rectifier circuit and drives the display means.

5. The combination as defined in claim 4, wherein the electrical control means further includes a transient squelch circuit electrically connected to the damping and biasing circuit for blocking signal transients when power is applied to the system which are caused by momentary instabilities of the system.

6. The combination as defined in claim 4, wherein the electrical control means further includes a square wave generator electrically connected to said first selector means for checking the operation of the control unit and model module.

7. A helicopter rotor system related vibration amplitude detecting system, comprising in combination:
at least one vibration amplitude sensing device, mounted to the helicopter in the vibrational sphere of the rotor system related vibration, said sensing device generating a signal which is indicative of the amplitude of the rotor system related vibration;
a control unit including: first and second selector means; said second selector means serving to selectively, electrically connect each sensing device to said first selector means, said first selector means serving to selectively receive the generated signal from each sensing device; electrical control means for operating on the selected generated signal and producing an output signal within a selected frequency and amplitude range; and display means for displaying indicia of the output signal; and
a model module electrically connected to said second selector means and having fixed and variable resistors which are preset as a function of the dynamic rotor system of the helicopter and which are selectively applied to the electrical control means by said second selector means.

8. The combination as defined in claim 7, wherein the electrical control means includes filter means, electrically connected to said first selector means for receiving the generated signal of a selected sensing device and to said second selector means for adapting the filter means to the dynamic rotor system of the helicopter.

9. The combination as defined in claim 8, wherein the electrical control means further includes: a scaling amplifier electrically connected to said second selector means and thereby to a variable resistor in the model module for controlling the gain thereof, said scaling amplifier receiving the output from said filter means; a full-wave rectifier circuit which receives the output from said scaling amplifier; and a damping and biasing circuit which receives the output from the rectifier circuit and drives the display means.

10. The combination as defined in claim 9, wherein the electrical control means further includes a transient squelch circuit electrically connected to the damping and biasing circuit for blocking signal transients when power is applied to the system which are caused by momentary instabilities of the system.

11. The combination as defined in claim 9, wherein the electrical control means further includes a square wave generator electrically connected to said first selector means for checking the operation of the control unit and model module.

12. A helicopter rotor system related vibration detecting system, comprising in combination:
at least one vibration amplitude sensing device mounted to the helicopter in the vibrational sphere of the rotor system related vibration, said sensing device including two accelerometers mounted with their sensitive axes at right angles and generating a signal which is indicative of the amplitude of the rotor system related vibration;
a control unit having a housing including: a first multi-position switch; a connection for each sensing device for electrically connecting each sensing device to said first multi-position switch, said first multi-position switch serving to selectively receive the generated signal from each sensing device; electrical control means for operating on the selected generated signal and producing an output signal within a selected frequency and amplitude range; display means for displaying indicia of the output signal; a receiving slot for a model module; mounting means and a connector within the receiving slot; and a plurality of second multi-position switches; and
a model module having a housing which is received within the receiving slot, said model module housing including: mounting means which engage the control unit mounting means for securing the model module to the control unit; a connector which engages the control unit connector for electrically connecting the model module to the plurality of first and second multi-position switches; and a plurality of resistors preset as a function of the dynamic rotor system of the helicopter and selectively applied to the electrical control means by respective ones of the plurality of first and second multi-position switches for determining the selected frequency and amplitude range.

13. The combination as defined in claim 12, wherein the electrical control means includes a tuned band-pass filter, electrically connected to said first multi-position switch for receiving the generated signal of a selected sensing device and to certain ones of said plurality of second multi-position switches for adapting the tuned band-pass filter to the dynamic rotor system of the helicopter.

14. The combination as defined in claim 13, wherein the electrical control means further includes: a scaling amplifier, electrically connected to certain ones of said plurality of first and second multi-position switches and thereby to a variable resistor in the model module for controlling the gain thereof, said scaling amplifier receiving the output from said tuned band-pass filter; a full-wave rectifier circuit which receives the output from said scaling amplifier; and a damping and biasing circuit which receives the output from the rectifier circuit and drives the display means.

15. The combination as defined in claim 14, wherein the electrical control means further includes a transient squelch circuit electrically connected to the damping and biasing circuit for blocking signal transients when power is applied to the system which are caused by momentary instabilities of the system.

16. The combination as defined in claim 14, wherein the electrical control means further includes: a third multi-position switch; and a square wave generator elevtrically connected to said third multi-position switch for checking the operation of the control unit and model module.

* * * * *